US010722136B2

(12) United States Patent
Bouton (10) Patent No.: US 10,722,136 B2
(45) Date of Patent: Jul. 28, 2020

(54) WIRELESS AND POWER-SOURCE-FREE EXTRAVASATION AND INFILTRATION DETECTION SENSOR

(75) Inventor: Chad E. Bouton, Powell, OH (US)

(73) Assignee: Battelle Memorial Institute, Columbus, OH (US)

(*) Notice: Subject to any disclaimer, the term of this patent is extended or adjusted under 35 U.S.C. 154(b) by 255 days.

(21) Appl. No.: 14/241,179

(22) PCT Filed: Aug. 29, 2012

(86) PCT No.: PCT/US2012/052801
§ 371 (c)(1),
(2), (4) Date: Mar. 11, 2014

(87) PCT Pub. No.: WO2013/033166
PCT Pub. Date: Mar. 7, 2013

(65) Prior Publication Data
US 2015/0011876 A1 Jan. 8, 2015

Related U.S. Application Data (60) Provisional application No. 61/530,436, filed on Sep. 2, 2011, provisional application No. 61/530,454, filed
(Continued)

(51) Int. Cl.
*A61B 5/05* (2006.01)
*A61M 5/168* (2006.01)
(Continued)

(52) U.S. Cl.
CPC .......... *A61B 5/0507* (2013.01); *A61B 5/0022* (2013.01); *A61B 5/0537* (2013.01);
(Continued)

(58) Field of Classification Search
CPC ... A61B 5/0507; A61B 5/7246; A61B 5/7203; A61B 5/4839; A61B 5/7282;
(Continued)

(56) References Cited

U.S. PATENT DOCUMENTS 3,657,656 A * 4/1972 Cooper .................... H01Q 3/34
342/371
3,779,079 A 12/1973 Snook
(Continued)

FOREIGN PATENT DOCUMENTS

CA 2470801 2/2003
CN 10048215 4/2009
(Continued)

OTHER PUBLICATIONS

Gupta, Vani; First Office Action, U.S. Appl. No. 14/241,203; dated Oct. 5, 2015; United States Patent and Trademark Office; Alexandria, VA.
(Continued)

*Primary Examiner* — Serkan Akar
(74) *Attorney, Agent, or Firm* — Stevens & Showalter LLP (57) ABSTRACT

A system detects extravasation or infiltration by segregating active components that drive a passive sensor for economical single use. A receiving antenna of the passive sensor receives a transmitted signal comprising RF electromagnetic power. A first circuit transmits a first portion of the received signal through a body portion. A sensor detects a resultant signal from the body portion. A second circuit combines a reference signal comprising a second portion of the received signal with the resultant signal so as to define an output signal. A transmit antenna transmits the output signal to a receiver.

10 Claims, 3 Drawing Sheets

Related U.S. Application Data on Sep. 2, 2011, provisional application No. 61/530,441, filed on Sep. 2, 2011.

(51) Int. Cl.

| | | |
|---|---|---|
| *A61B 5/053* | (2006.01) | |
| *A61B 8/08* | (2006.01) | |
| *A61B 5/00* | (2006.01) | |

(52) U.S. Cl.
CPC .......... *A61B 5/4839* (2013.01); *A61B 5/4875* (2013.01); *A61B 5/7203* (2013.01); *A61B 5/7246* (2013.01); *A61B 5/7282* (2013.01); *A61B 8/08* (2013.01); *A61M 5/16831* (2013.01); *A61M 5/16836* (2013.01); *A61B 5/4878* (2013.01); *A61B 5/6824* (2013.01); *A61M 2205/3317* (2013.01); *F04C 2270/041* (2013.01)

(58) Field of Classification Search
CPC ............... A61B 5/4875; A61B 5/4878; A61M 5/16831; A61M 5/16836
See application file for complete search history.

(56) References Cited

U.S. PATENT DOCUMENTS

| | | | |
|---|---|---|---|
| 3,951,136 A | 4/1976 | Wall | |
| 4,010,749 A | 3/1977 | Shaw | |
| 4,240,445 A | 12/1980 | Iskander et al. | |
| 4,329,689 A | 5/1982 | Yee | |
| 4,378,808 A | 4/1983 | Lichtenstein | |
| 4,488,559 A | 12/1984 | Iskander | |
| 4,572,182 A | 2/1986 | Royse | |
| 4,575,705 A | 3/1986 | Gotcher | |
| 4,637,929 A | 1/1987 | Quay | |
| 4,641,659 A | 2/1987 | Sepponen | |
| 4,647,281 A | 3/1987 | Carr | |
| 4,648,869 A | 3/1987 | Bobo, Jr. | |
| 4,653,501 A | 3/1987 | Cartmell et al. | |
| 4,667,679 A | 5/1987 | Sahota | |
| 4,690,149 A | 9/1987 | Ko | |
| 4,816,019 A | 3/1989 | Kamen | |
| 4,819,648 A | 4/1989 | Ko | |
| 4,877,034 A | 10/1989 | Atkins et al. | |
| 4,923,442 A | 5/1990 | Segall et al. | |
| 4,959,050 A | 9/1990 | Bobo, Jr. | |
| 4,971,068 A | 11/1990 | Sahi | |
| 4,993,409 A | 2/1991 | Grim | |
| 4,997,055 A | 3/1991 | Grady | |
| 5,001,436 A | 3/1991 | Scot et al. | |
| 5,026,348 A | 6/1991 | Venegas | |
| 5,184,620 A | 2/1993 | Cudahy et al. | |
| 5,191,795 A | 3/1993 | Fellingham et al. | |
| 5,255,683 A | 10/1993 | Monaghan | |
| 5,334,141 A | 8/1994 | Carr et al. | |
| 5,479,927 A | 1/1996 | Shmulewitz | |
| 5,628,322 A | 5/1997 | Mine | |
| 5,685,305 A | 11/1997 | Moonen et al. | |
| 5,769,784 A | 6/1998 | Barnett et al. | |
| 5,840,026 A | 11/1998 | Uber, III et al. | |
| 5,861,019 A | 1/1999 | Sun et al. | |
| 5,947,910 A | 9/1999 | Zimmet | |
| 5,954,668 A | 9/1999 | Uber, III et al. | |
| 5,957,950 A | 9/1999 | Mockros et al. | |
| 5,964,703 A | 10/1999 | Goodman et al. | |
| 5,995,863 A | 11/1999 | Farace et al. | |
| 6,026,173 A | 2/2000 | Svenson et al. | |
| 6,031,892 A | 2/2000 | Karellas | |
| 6,047,215 A | 4/2000 | McClure et al. | |
| 6,061,589 A | 5/2000 | Bridges et al. | |
| 6,233,476 B1 | 5/2001 | Strommer et al. | |
| 6,233,479 B1 | 5/2001 | Haddad et al. | |
| 6,251,073 B1 | 6/2001 | Imran et al. | |
| 6,263,226 B1 | 7/2001 | Axelgaard et al. | |
| 6,300,906 B1 | 10/2001 | Rawnick et al. | |
| 6,315,719 B1 | 11/2001 | Rode et al. | |
| 6,332,087 B1 | 12/2001 | Svenson et al. | |
| 6,367,023 B2 | 4/2002 | Kling et al. | |
| 6,375,624 B1 | 4/2002 | Uber, III et al. | |
| 6,385,483 B1 | 5/2002 | Uber, III et al. | |
| 6,397,098 B1 | 5/2002 | Uber, III et al. | |
| 6,408,204 B1 | 6/2002 | Hirschman | |
| 6,415,170 B1 | 7/2002 | Loutis et al. | |
| 6,425,878 B1* | 7/2002 | Shekalim | A61B 5/01 600/384 |
| 6,454,711 B1 | 9/2002 | Haddad et al. | |
| 6,459,931 B1 | 10/2002 | Hirschman | |
| 6,487,428 B1 | 11/2002 | Culver et al. | |
| 6,520,930 B2 | 2/2003 | Critchlow et al. | |
| 6,587,428 B2 | 7/2003 | Kuribayashi | |
| 6,673,033 B1 | 1/2004 | Sciulli et al. | |
| 6,704,592 B1 | 3/2004 | Reynolds et al. | |
| 6,751,500 B2 | 6/2004 | Hirschman | |
| 6,970,735 B2 | 11/2005 | Uber, III et al. | |
| 7,047,058 B1 | 5/2006 | Dvorsky et al. | |
| 7,077,832 B2 | 7/2006 | Fleischmann | |
| 7,122,012 B2 | 10/2006 | Bouton et al. | |
| 7,221,159 B2 | 5/2007 | Griffiths et al. | |
| 7,226,415 B2* | 6/2007 | Haddad | A61B 5/05 600/371 |
| 7,283,860 B2 | 10/2007 | Frazier et al. | |
| 7,431,728 B2 | 10/2008 | Gerry et al. | |
| 7,457,804 B2 | 11/2008 | Uber, III et al. | |
| 7,532,953 B2 | 5/2009 | Vogel | |
| 7,591,792 B2 | 9/2009 | Bouton | |
| 7,627,710 B1 | 12/2009 | Todd et al. | |
| 7,632,245 B1 | 12/2009 | Cowan et al. | |
| 7,674,244 B2 | 3/2010 | Kalafut et al. | |
| 7,713,239 B2 | 5/2010 | Uber, III et al. | |
| 7,937,134 B2 | 5/2011 | Uber et al. | |
| 7,996,381 B2 | 8/2011 | Uber, III et al. | |
| 8,055,328 B2 | 11/2011 | Uber, III et al. | |
| 8,096,957 B2 | 1/2012 | Conquergood et al. | |
| 8,160,679 B2 | 4/2012 | Uber et al. | |
| 8,182,444 B2 | 5/2012 | Uber, III et al. | |
| 8,192,397 B2 | 6/2012 | Griffiths et al. | |
| 8,295,920 B2 | 10/2012 | Bouton et al. | |
| 8,307,693 B2 | 11/2012 | Uram et al. | |
| 8,323,240 B2 | 12/2012 | Wulfman et al. | |
| 8,352,015 B2 | 1/2013 | Bernstein et al. | |
| 8,388,582 B2 | 3/2013 | Eubanks et al. | |
| 8,454,561 B2 | 6/2013 | Uber, III et al. | |
| 8,521,716 B2 | 8/2013 | Uber, III et al. | |
| 8,630,718 B2 | 1/2014 | Stahmann et al. | |
| 9,289,550 B1 | 3/2016 | Dvorsky et al. | |
| 2001/0044588 A1 | 11/2001 | Mault | |
| 2002/0040193 A1 | 4/2002 | Hirschman | |
| 2002/0049375 A1 | 4/2002 | Strommer et al. | |
| 2002/0123674 A1 | 9/2002 | Plicchi et al. | |
| 2002/0172323 A1 | 11/2002 | Karellas et al. | |
| 2003/0004433 A1 | 1/2003 | Hirschman | |
| 2003/0036674 A1* | 2/2003 | Bouton | A61B 5/05 600/12 |
| 2003/0036713 A1* | 2/2003 | Bouton | A61B 5/05 600/587 |
| 2003/0120170 A1 | 6/2003 | Zhu et al. | |
| 2004/0086734 A1 | 5/2004 | Janssens et al. | |
| 2004/0162488 A1 | 8/2004 | Uber, III et al. | |
| 2004/0225255 A1 | 11/2004 | Ono | |
| 2005/0015009 A1 | 1/2005 | Mourad et al. | |
| 2005/0073424 A1* | 4/2005 | Ruoss | A61B 5/0507 340/686.6 |
| 2005/0234428 A1 | 10/2005 | Spohn et al. | |
| 2006/0025897 A1* | 2/2006 | Shostak | B60C 23/005 701/1 |
| 2006/0122497 A1 | 6/2006 | Glossop | |
| 2006/0135884 A1 | 6/2006 | Hack et al. | |
| 2006/0211970 A1 | 9/2006 | Sciulli | |
| 2006/0213234 A1 | 9/2006 | Gladfelter et al. | |
| 2006/0213249 A1 | 9/2006 | Uram et al. | |
| 2007/0010702 A1 | 1/2007 | Wang et al. | |
| 2007/0056871 A1 | 3/2007 | Griffiths et al. | |
| 2007/0123770 A1 | 5/2007 | Bouton et al. | |

(56) References Cited

U.S. PATENT DOCUMENTS

| | | |
|---|---|---|
| 2007/0225601 A1 | 9/2007 | Uber, III et al. |
| 2007/0225637 A1 | 9/2007 | Ono et al. |
| 2007/0244428 A1 | 10/2007 | Uram et al. |
| 2007/0276327 A1 | 11/2007 | Kalafut et al. |
| 2007/0282198 A1 | 12/2007 | Uber, III et al. |
| 2007/0282199 A1 | 12/2007 | Uber, III et al. |
| 2008/0058680 A1 | 3/2008 | Lee et al. |
| 2008/0058758 A1 | 3/2008 | Ranchod et al. |
| 2008/0097339 A1 | 4/2008 | Ranchod et al. |
| 2008/0166292 A1 | 7/2008 | Levin et al. |
| 2008/0167900 A1 | 7/2008 | Ranchod |
| 2008/0195060 A1 | 8/2008 | Roger et al. |
| 2008/0294096 A1 | 11/2008 | Uber, III et al. |
| 2008/0319285 A1 | 12/2008 | Hancock |
| 2009/0015353 A1* | 1/2009 | Rofougaran ....... G06K 7/10237 333/24 C |
| 2009/0070342 A1 | 3/2009 | Uber, III et al. |
| 2009/0177050 A1 | 7/2009 | Griffiths et al. |
| 2009/0247866 A1 | 10/2009 | Uber, III et al. |
| 2009/0276327 A1 | 11/2009 | Malik |
| 2009/0299175 A1 | 12/2009 | Bernstein et al. |
| 2009/0326370 A1 | 12/2009 | Uber, III et al. |
| 2010/0049004 A1 | 2/2010 | Edman et al. |
| 2010/0113887 A1 | 5/2010 | Kalafut et al. |
| 2010/0114064 A1 | 5/2010 | Kalafut et al. |
| 2010/0160786 A1 | 6/2010 | Nordgren et al. |
| 2010/0174179 A1* | 7/2010 | Persson ................ A61B 5/05 600/430 |
| 2010/0185040 A1 | 7/2010 | Uber, III et al. |
| 2010/0198141 A1 | 8/2010 | Laitenberger et al. |
| 2010/0256462 A1 | 10/2010 | Rappaport et al. |
| 2011/0002802 A1 | 1/2011 | Capone et al. |
| 2011/0130800 A1 | 6/2011 | Weinstein et al. |
| 2011/0257522 A1 | 10/2011 | Berard-Andersen et al. |
| 2012/0019386 A1* | 1/2012 | Doraiswami .... G01N 33/48792 340/573.1 |
| 2013/0062528 A1 | 3/2013 | Hyde et al. |
| 2013/0079581 A1 | 3/2013 | Agamaite et al. |
| 2013/0123567 A1 | 5/2013 | Agamaite et al. |
| 2013/0123614 A1 | 5/2013 | Bernstein et al. |
| 2013/0131585 A1 | 5/2013 | Eubanks et al. |
| 2013/0190646 A1 | 7/2013 | Weinstein et al. |
| 2013/0231550 A1 | 9/2013 | Weinstein et al. |
| 2013/0253254 A1 | 9/2013 | Uber, III et al. |
| 2013/0255390 A1 | 10/2013 | Riley et al. |
| 2013/0274599 A1 | 10/2013 | Bouton et al. |
| 2013/0331634 A1 | 12/2013 | Kaintz et al. |
| 2013/0331635 A1 | 12/2013 | Hoffman et al. |
| 2013/0331810 A1 | 12/2013 | Bazala et al. |
| 2013/0345676 A1 | 12/2013 | Wulfman et al. |
| 2014/0046295 A1 | 2/2014 | Uber, III et al. |
| 2014/0228686 A1 | 8/2014 | Bouton |

FOREIGN PATENT DOCUMENTS

| | | |
|---|---|---|
| DE | 4007587 | 9/1991 |
| EP | 1472973 | 11/2004 |
| EP | 1647306 | 4/2006 |
| EP | 2455402 | 5/2012 |
| EP | 2526857 | 11/2012 |
| EP | 2750594 | 7/2014 |
| EP | 2750595 | 7/2014 |
| GB | 2251080 | 6/1992 |
| JP | 1157001 | 3/1999 |
| JP | 2007509353 | 4/2007 |
| WO | 9926685 | 6/1999 |
| WO | 9926686 | 6/1999 |
| WO | 9929356 | 6/1999 |
| WO | 0108729 | 2/2001 |
| WO | 2003000972 A1 | 1/2003 |
| WO | 03009752 | 2/2003 |
| WO | 03063680 | 8/2003 |
| WO | 2004036467 | 4/2004 |
| WO | 2005043100 | 5/2005 |
| WO | 03009753 | 2/2006 |
| WO | 2008100670 | 8/2008 |
| WO | 2009009753 A1 | 1/2009 |
| WO | 20100146372 | 12/2010 |
| WO | 2011067623 | 6/2011 |
| WO | 2011067685 | 6/2011 |
| WO | 2012011065 | 1/2012 |
| WO | 2012011066 | 1/2012 |
| WO | 2012059929 | 5/2012 |
| WO | 2013033162 | 3/2013 |
| WO | 2013033166 | 3/2013 |
| WO | 2013033174 | 3/2013 |
| WO | 2013093923 | 6/2013 |
| WO | 2013147799 | 10/2013 |

OTHER PUBLICATIONS

Gupta, Vani; First Office Action, U.S. Appl. No. 14/241,171; dated Sep. 10, 2015; United States Patent and Trademark Office; Alexandria, VA.

Carr, Kenneth L.; Use of Gallium Arsenide in Medical Applications: Microwave Medical Systems, Inc.; GaAs IC Symposium; pp. 10-13; 1999 IEEE.

Shaeffer, James et al.; Early Detection of Extravasation of Radiographic Contrast Medium; Radiology; pp. 141-144; Jul. 1992.

Gupta, Vani; Final Office Action; U.S. Appl. No. 14/241,203; dated May 6, 2016; United States Patent and Trademark Office, Alexandria, VA.

Gupta, Vani; Office Action; U.S. Appl. No. 14/241,171; dated Mar. 2, 2016; United States Patent and Trademark Office, Alexandria, VA.

Chad E. Bouton; U.S. Appl. No. 14/241,171, filed Mar. 11, 2014 entitled Distributed Extravasation Detection System; United States Patent and Trademark Office; Alexandria, VA (National Stage of PCT/US2012/052796 filed Aug. 29, 2012).

De la Hera, German; International Search Report and Written Opinion; International Application No. PCT/US2012/052796; dated Dec. 10, 2012; European Patent Office.

De la Hera, German; International Search Report and Written Opinion; International Application No. PCT/US2012/052801; dated Dec. 19, 2012; European Patent Office.

De la Hera, German; International Search Report and Written Opinion; International Application No. PCT/US2012/052813; dated Dec. 7, 2012; European Patent Office.

Shaeffer, James et al.; Detection of Extravasation of Antineoplastic Drugs by Microwave Radiometry; Cancer Letter, 31; pp. 284-291; 1986; Elsevier Scientific Publishers Ireland Ltd.

Sukamto, Lin M. et al.; MMIC Receiver for Water-Vapor Radiometer; NASA Tech Briefs; p. 34; Sep. 1993.

Arkin, H. et al.; Recent Developments in Modeling Heat Transfer in Blood Perfused Tissues; IEEE Transactions on Biomedical Engineering; vol. 41, No. 2; pp. 97-107; Feb. 1994.

Harris, Thomas S. et al.; Infusion Line Model for the Detection of Infiltration Extravasation, and other Fluid Flow Faults; IEEE Transactions on Biomedical Engineering; vol. 40, No. 2; pp. 154-162; Feb. 1993.

Montreuil, Jean et al.; Multiangle Method for Temperature Measurement of Biological Tissues by Microwave Radiometry; IEEE Transactions on Microwave Theory and Techniques; vol. 39, No. 7; pp. 1235-1238; Jul. 1991.

Lin, James C. et al.; Microwave Imaging of Cerebral Edema; Proceedings of the IEEE; vol. 70, No. 5; pp. 523-524; May 1982.

Kramer, Gerhard G. et al.; Dielectric Measurement of Cerebral Water Content Using a Network Analyzer; Neurological Research; vol. 14, No. 3; pp. 255-258; Sep. 1992.

Ling, Geoffrey S.F. et al.; Diagnosis of Subdural and Intraparenchymal Intracranial Hemorrhage Using a Microwave Based Detector; Digitization of the Battlespace V and Battlefield Biomedical Technologies II; vol. 4037; pp. 212-217; Apr. 24, 2000.

Behari, J. et al.; Dielectric Permittivity of Biological Tissues in the Microwave Frequency Range; Proceedings of the SPIE—The Inter- (56) References Cited

OTHER PUBLICATIONS national Society for Optical Engineering, Advanced Microwave and Millimeter-Wave Detectors; vol. 2275; pp. 301-308; San Diego, CA; Jul. 25-26, 1994.
Andreuccetti, D. et al.; High Permittivity Patch Radiator for Single and Multi-Element Hyperthermia Applicators; IEEE Transactions on Biomedical Engineering; vol. 40, No. 7; pp. 711-715; IEEE Inc.; New York; Jul. 1, 1993.
Lee, Eric R. et al.; Body Conformable 915 MHz Microstrip Array Applicators for Large Surface Area Hyperthermia; IEEE Transactions on Biomedical Engineering; vol. 39, No. 5; pp. 470-438; IEEE Inc., New York; May 1, 1992.
Jameson, P.; International Search Report; Application No. PCT/US00/20112; dated Oct. 17, 2000; European Patent Office.
Van Dooren, G.; International Search Report; Application No. PCT/US02/23877; dated Feb. 6, 2003; European Patent Office.
Beitner, M.; International Search Report; Application No. PCT/US02/23925; dated Jan. 15, 2003; European Patent Office.
P.B. James and R.W. Galloway; The Ultrasonic Blood Velocity Detector as an Aid to Arteriography; Br J Radiol; Oct. 1971; 44:743-746.
European Search Report for EP12005361 dated Mar. 6, 2013.
Bouton, Chad E.: Final Office Action; U.S. Appl. No. 13/620,310; dated Jan. 6, 2014; United States Patent and Trademark Office; Alexandria, VA.
Supplementary European Search Report for EP04796177 dated May 11, 2010.
Partial European Search Report for EP12005361 dated Nov. 2, 2012.
Kent: "Hand-Held Instrument for Fat/Water Determination in Whole Fish"; 1993; at http://distell.com/products/prd-fish-fatmeter/technical-data/ffm-research-paper.
Birnbaum et al.: "Extravasation Detection Accessory: Clinical Evaluation in 500 Patients"; 1999; Radiology 212:431-438.
"Value of Multi-Detector Array CT in the Assessment of Portal Hypertension"; Portal Hypertension: Diagnostic Imaging and Imaging-Guided Therapy (Medical Radiology/Diagnostic Imaging).; Ed. Plinio Rossi. 1st ed.; Springer; 2000; p. 111.
International Preliminary Report on Patentability and Written Opinion dated Oct. 5, 2005 for PCT/US2004/35135.
International Search Report for PCT/US2004/035135 dated Oct. 5, 2005.
Gupta, Vani; Office Action; U.S. Appl. No. 14/241,171; dated Jun. 17, 2016; United States Patent and Trademark Office, Alexandria, VA.
Gupta, Vani; Office Action; U.S. Appl. No. 14/241,171; dated Dec. 16, 2016; United States Patent and Trademark Office, Alexandria, VA.
Gupta, Vani; Office Action; U.S. Appl. No. 14/241,203; dated Aug. 30, 2016; United States Patent and Trademark Office, Alexandria, VA.
Gupta, Vani; Office Action; U.S. Appl. No. 14/241,171; dated Jul. 25, 2017; United States Patent and Trademark Office, Alexandria, Virginia.
Ip, Jason M.; Final Office Action; U.S. Appl. No. 13/620,310; dated Mar. 5, 2018; United States Patent and Trademark Office; Alexandria, VA.
Ip, Jason M.; Office Action; U.S. Appl. No. 13/620,310; dated Jul. 27, 2017; United States Patent and Trademark Office; Alexandria, VA.
Ip, Jason M.; Final Office Action; U.S. Appl. No. 13/620,310; dated Jun. 14, 2016; United States Patent and Trademark Office; Alexandria, VA.
Ip, Jason M.; Advisory Action; U.S. Appl. No. 13/620,310; dated May 5, 2016; United States Patent and Trademark Office; Alexandria, VA.
Ip, Jason M.; Final Office Action; U.S. Appl. No. 13/620,310; dated Feb. 5, 2016; United States Patent and Trademark Office; Alexandria, VA.
Ip, Jason M.; Office Action; U.S. Appl. No. 13/620,310; dated May 29, 2015; United States Patent and Trademark Office; Alexandria, VA.
Ip, Jason M.; Final Office Action; U.S. Appl. No. 13/620,310; dated Aug. 7, 2014; United States Patent and Trademark Office; Alexandria, VA.
Ip, Jason M.; Office Action; U.S. Appl. No. 13/620,310; dated Apr. 23, 2014; United States Patent and Trademark Office; Alexandria, VA.
Ip, Jason M.; Office Action; U.S. Appl. No. 13/620,310; dated Sep. 9, 2013; United States Patent and Trademark Office; Alexandria, VA.
Bor, Helene Catherine; Notice of Allowance; U.S. Appl. No. 11/385,448; dated Nov. 20, 2015; United States Patent and Trademark Office; Alexandria, VA.
Bor, Helene Catherine; Final Office Action; U.S. Appl. No. 11/385,448; dated Jun. 3, 2015; United States Patent and Trademark Office; Alexandria, VA.
Bor, Helene Catherine; Office Action; U.S. Appl. No. 11/385,448; dated Sep. 30, 2014; United States Patent and Trademark Office; Alexandria, VA.
Bor, Helene Catherine; Office Action; U.S. Appl. No. 11/385,448; dated Jan. 6, 2014; United States Patent and Trademark Office; Alexandria, VA.
Bor, Helene Catherine; Final Office Action; U.S. Appl. No. 11/385,448; dated Jul. 18, 2013; United States Patent and Trademark Office; Alexandria, VA.
Bor, Helene Catherine; Office Action; U.S. Appl. No. 11/385,448; dated Dec. 28, 2012; United States Patent and Trademark Office; Alexandria, VA.
Bor, Helene Catherine; Advisory Action; U.S. Appl. No. 11/385,448; dated Aug. 29, 2011; United States Patent and Trademark Office; Alexandria, VA.
Fontenot, Nigel Rai; Final Office Action; U.S. Appl. No. 11/385,448; dated Mar. 28, 2011; United States Patent and Trademark Office; Alexandria, VA.
Fontenot, Nigel Rai; Office Action; U.S. Appl. No. 11/385,448; dated Dec. 3, 2010; United States Patent and Trademark Office; Alexandria, VA.
Fontenot, Nigel Rai; Final Office Action; U.S. Appl. No. 11/385,448; dated Feb. 24, 2010; United States Patent and Trademark Office; Alexandria, VA.
Fontenot, Nigel Rai; Office Action; U.S. Appl. No. 11/385,448; dated Sep. 30, 2009; United States Patent and Trademark Office; Alexandria, VA.
Fontenot, Nigel Rai; Final Office Action; U.S. Appl. No. 11/385,448; dated May 13, 2009; United States Patent and Trademark Office; Alexandria, VA.
Fontenot, Nigel Rai; Office Action; U.S. Appl. No. 11/385,448; dated Nov. 13, 2008; United States Patent and Trademark Office; Alexandria, VA.
Gupta, Vani; Non-final Office Action; U.S. Appl. No. 14/241,203; dated Mar. 13, 2018; United States Patent and Trademark Office, Alexandria, Virginia.
Gupta, Vani; Final Office Action; U.S. Appl. No. 14/241,203; dated Apr. 21, 2017; United States Patent and Trademark Office, Alexandria, VA.
Gupta, Vani; Office Action; U.S. Appl. No. 14/241,203; dated Nov. 2, 2018; U.S. Patent and Trademark Office; Alexandria, VA.
Gupta, Vani; Final Office Action; U.S. Appl. No. 14/241,171; dated May 29, 2018; United States Patent and Trademark Office; Alexandria, VA.
De la Hera, Germán; Examination Report; European Patent Application No. 12772147.0; dated Oct. 8, 2018; European Patent Office, Munich, Germany.
De la Hera, German; Office Action; European Patent Application No. 12759562.7; dated Oct. 5, 2018; European Patent Office, Munich, Germany.
Gupta, Vani; Office Action; U.S. Appl. No. 14/241,171; dated Mar. 20, 2019; U.S. Patent and Trademark Office; Alexandria, VA.
Akar, Serkan; Final Office Action; U.S. Appl. No. 14/241,171; dated Aug. 28, 2019; U.S. Patent and Trademark Office; Alexandria, VA.

(56) References Cited

OTHER PUBLICATIONS

Akar, Serkan; Office Action; U.S. Appl. No. 14/241,203; dated Aug. 23, 2019; U.S. Patent and Trademark Office; Alexandria, VA.
EPO Examination Report; European Patent Application No. 12759562.7; dated Feb. 4, 2020; European Patent Office; Munich, Germany.

* cited by examiner

WIRELESS AND POWER-SOURCE-FREE EXTRAVASATION AND INFILTRATION DETECTION SENSOR

TECHNICAL FIELD

The present invention relates generally to the detection of fluids in tissue, and, more particularly, to apparatuses, systems and methods for detection of changed, elevated or abnormal fluid levels in tissue.

BACKGROUND ART

Changed, elevated or abnormal fluid levels in living tissue can result from a number of physiological conditions. For example, edema is an abnormal accumulation of watery fluid in the intercellular spaces of connective tissue. Edematous tissues are swollen and, when punctured, secrete a thin incoagulable fluid. Edema is most frequently a symptom of disease rather than a disease in itself, and it may have a number of causes, most of which can be traced back to gross variations in the physiological mechanisms that normally maintain a constant water balance in the cells, tissues, and blood. Among the causes may be diseases of the kidneys, heart, veins, or lymphatic system; malnutrition; or allergic reactions.

Moreover, bleeding (hemorrhage) can cause blood to collect and clot (hematoma). Hematomas can, for example, occur beneath the outermost of three membranes that cover the brain (meninges) as a result of a head injury. There are two types of cranial subdural hematomas. An acute subdural hematoma occurs soon after a severe head injury. A chronic subdural hematoma is a complication that may develop weeks after a head injury. Such a head injury may have been so minor that the patient does not remember it. An epidural hematoma is a traumatic accumulation of blood between the inner table of the skull and the stripped-off dural membrane. The inciting event often is a focused blow to the head. It is often difficult to detect hematomas, particularly when the hematoma occurs well after the time of an injury.

In addition to accumulation of body fluids, elevated fluid levels in tissue can arise as a result of introduction of a fluid into the body, for example, during an injection procedure. In that regard, in many medical diagnostic and therapeutic procedures, a physician or other person injects fluid into a patient's blood vessels. Moreover, in recent years, a number of injector-actuated syringes and powered injectors for pressurized injection of contrast medium in procedures such as angiography, computed tomography, ultrasound and NMR/MRI (Nuclear Magnetic Resonance/Magnetic Resonance Imaging) have been developed.

Extravasation or infiltration is the accidental infusion or leakage of an injection fluid such as a contrast medium or a therapeutic agent into tissue surrounding a blood vessel rather than into the blood vessel itself. Extravasation can be caused, for example, by rupture or dissection of fragile vasculature, valve disease, inappropriate needle placement, or patient movement resulting in the infusing needle being pulled from the intended vessel or causing the needle to be pushed through the wall of the vessel. High injection pressures and/or rates of some modern procedures can increase the risk of extravasation. In computed tomography, for example, contrast injection flow rates can be in the range of 0.1 to 10 ml/s.

Extravasation can cause serious injury to patients. In that regard, certain injection fluids such as contrast media or chemotherapy drugs can be toxic to tissue. It is, therefore, very important when performing fluid injections to detect extravasation as soon as possible and discontinue the injection upon detection.

In U.S. Pat. No. 7,122,012 to Bouton, et al., issued Oct. 17, 2006, which is hereby incorporated by reference in its entirety, a method was disclosed for detecting a change in the level of fluid in tissue in a first area of a body. Steps included applying electromagnetic energy, preferably in the frequency range of approximately 300 MHz to approximately 30 GHz, to a first volume of the body; measuring a resultant or returned signal; comparing the signal to a reference signal to determine if the fluid level in the tissue has changed. In one embodiment, the method detected changes in the level of fluid in tissue of a body by applying electromagnetic energy to a first volume of the body over a period of time; measuring a resultant signal or a signal returned from the tissue; and comparing the signal to a reference signal to determine if a level of fluid in the tissue has changed during the period of time.

DISCLOSURE OF INVENTION

The following presents a summary in order to provide a basic understanding of some aspects of the disclosed aspects. This summary is not an extensive overview and is intended to neither identify key or critical elements nor delineate the scope of such aspects. Its purpose is to present some concepts of the described features in a form as a prelude to the more detailed description that is presented later.

In accordance with one or more aspects and embodiments, and the corresponding disclosures thereof, various features of the invention are described in connection with a wireless and passive sensor (no local power source is required on the sensor) of a system for detecting extravasation or infiltration. By segregating active components that drive the passive sensor via Radio Frequency (RF) transmission, the passive sensor can be economically disposed of after use. Thereby, health protocols in an institutional setting can be enhanced. Moreover, the passive sensor allows a degree of mobility for a wearer by being linked via the RF transmission.

In a first aspect, the present invention provides a passive sensor that comprises a receiving antenna for receiving a transmitted signal comprising RF electromagnetic power as a received signal. A first circuit transmits a first portion of the received signal through a body portion. A sensor detects a resultant signal from the body portion. A second portion of the received signal defining a reference signal passes through a reference pathway that is not affected by fluid or other changes in the tissue. The combination of the signal that has passed through the body portion, i.e., the resultant signal and the reference signal defines an output signal. A transmit antenna transmits the output signal to a receiver for use in determining a change in a level of fluid in the body portion.

In a second aspect, the present invention provides a system for detecting extravasation that comprises a sensor according to the first aspect of the invention. In some embodiments, the system of the invention may comprise a signal generator for transmitting a transmitted signal comprising RF electromagnetic power selected for being transmittable through a body portion in relation to an amount of fluid in the body portion due to extravasation. A passive sensor comprises a receiving antenna for receiving the transmitted signal as a received signal, a first circuit for transmitting a first portion of the received signal through the body portion, a sensor for detecting a resultant signal from the body portion, a second circuit for combining a reference signal comprising a second portion of the received signal with the resultant signal so as to define an output signal, and a transmit antenna for transmitting the output signal. A signal processor may then receive the transmitted output signal for use in determining a change in fluid level in the body portion.

In some embodiments, the signal processor further performs a ratio comparison of peak amplitude of the resultant signal and the reference signal of the transmitted output signal.

In other embodiments, the signal generator may use a series of time domain pulses of electromagnetic power. The passive sensor may further comprises a first delay circuit for delaying a selected one of the first portion of the received signal comprising the time domain pulse and the second portion of the received signal comprising the time domain pulse as the reference signal. In a particularly suitable embodiment, a second delay circuit delays the other one of the first portion and the second portion of the time domain pulse. The first and second delay circuits may be configured to separate in time the resultant signal and the reference signal from each other as well as a noise pulse at the sensor arising due to a reflected portion of the transmitted signal.

In further embodiments, the receiving antenna further receives the transmitted signal predominantly in a range of greater than 1.5 GHz to approximately 30 GHz over a period of time. In a particular aspect, the range is less than 10 GHz.

In some embodiments, the transmitted signal may comprise a sweep of continuous wave electromagnetic power across a frequency range.

In further embodiments, a substrate is provided to support one or more, and suitable each of the receiving antenna, the first circuit for transmitting, the second circuit for combining, the sensor, and the transmit antenna.

In a third aspect, the present disclosure provides a method for detecting extravasation. A transmitted signal is transmitted comprising RF electromagnetic power selected for being transmittable through a body portion in relation to an amount of fluid in the body portion due to extravasation. The transmitted signal is received as a received signal. A first portion of the received signal is transmitted through the body portion. A resultant signal is detected from the body portion. A reference signal comprising a second portion of the received signal is combined with the resultant signal so as to define an output signal. The output signal is transmitted. The transmitted output signal is received. The output signal is used to determine a change in fluid level in the body portion. In a particularly suitable embodiment of this aspect, the method may be performed using a device, apparatus / system according to the invention.

In some embodiments, a ratio comparison of peak amplitude of the resultant signal and the reference signal is performed.

In another embodiment, the transmitted signal may further comprise a time domain pulse of electromagnetic power. The method further may further comprise delaying a selected one of the first portion of the received signal comprising the time domain pulse and a second portion of the received signal comprising the time domain pulse as the reference signal. The reference signal is combined with the resultant signal as pulses separated as a function of time. In a particularly suitable embodiments, the other one of the first portion and the second portion of the time domain pulse is delayed to separate in time the resultant signal and the reference signal from each other as well as blanking a noise pulse arising due to a reflected portion of the transmitted signal from an ambient environment.

In an additional embodiment, the transmitted signal may be transmitted in a range of greater than 1.5 GHz to approximately 30 GHz over a period of time. In a particularly embodiment, the range is less than 10 GHz.

To the accomplishment of the foregoing and related ends, one or more aspects comprise the features hereinafter fully described and particularly pointed out in the claims. The following description and the annexed drawings set forth in detail certain illustrative aspects and are indicative of but a few of the various ways in which the principles of the aspects may be employed. Other advantages and novel features will become apparent from the following detailed description when considered in conjunction with the drawings and the disclosed aspects are intended to include all such aspects and their equivalents.

BRIEF DESCRIPTION OF DRAWINGS

The disclosed aspects will hereinafter be described in conjunction with the appended drawings, provided to illustrate and not to limit the disclosed aspects, wherein like designations denote like elements, and in which.

MODES FOR CARRYING OUT THE INVENTION

While the sensors, systems and methods of the present invention are generally applicable to the sensing of a wide range of fluids within a variety of body tissues (whether a body fluid or an introduced fluid), the present invention is primarily described herein with reference to the representative example of extravasation of a fluid intended to be injected into a vascular structure. However, one skilled in the art with the benefit of the present disclosure can appreciate that elevated, abnormal or changing levels of generally any fluid can be detected using the sensors, systems and methods of the present invention. Detection of body fluids in the present invention includes, but is not limited to, the detection of fluid changes as a result of edema, hematoma, ruptured bowel and colostomy tubing leakage into the peritoneal cavity. Introduced or foreign fluid detectible in the present invention include fluid introduced via generally any technique known in the medical arts including, but not limited to, injection, infusion and IV drip. Changes in complex permittivity and permeability as a result of changing fluid levels in tissue are detected by application of electromagnetic power to the tissue and detection of a resultant signal.

Complex permittivity and permeability govern how an electromagnetic wave will propagate through a substance. Complex permittivity typically has the greatest effect since it varies significantly between tissue types and fluids of interest. The complex permeability of various tissues and many fluids of interest is approximately that of a vacuum, reducing the effect of this parameter. However, some fluids such as MRI contrast agents may have an appreciable complex permeability difference from tissue. Although blood contains small amounts of iron, the permeability value for any significant volume of blood is typically insignificant. Complex permittivity is generally expressed as $$\varepsilon^* = \varepsilon' - j\varepsilon''$$

wherein ε' is the real component of the complex value and is known as the dielectric constant or sometimes simply referred to as the "permittivity." The term ε" is the imaginary component of the complex value and is often referred to as the "loss factor." The ratio of ε"/ε' is known as the "loss tangent." The complex permittivity (and sometimes permeability) of certain substances differ from the body tissue at certain frequencies. In the present invention, such differences in permittivity and/or permeability are used for the detection and level monitoring of certain fluids and substances in biological tissue.

The studies of the present innovation have shown that electromagnetic power having, for example, a frequency in the range of approximately 300 MHz to approximately 30 GHz (and, more preferably, in the range of approximately 1 GHz to approximately 10 GHz, and, even more preferably, in the range of approximately 3 GHz to approximately 5 GHz to 10 GHz) provides good penetration into tissue. In general, such electromagnetic power is launched into the subcutaneous tissue and a resultant signal is measured. Electromagnetic power in the frequency range set forth above has been found to transmit through the skin and to transmit or propagate well within, for example, fat. Good transmission through the fat layer is beneficial for detection of extravasation as many extravasations occur in the fat layer. The sensitivity to extravasation of the systems, devices and methods of the present invention is thus increased as compared, for example, to impedance plethysmography. In the case of impedance plethysmography, the majority of the electrical current passes through highly conductive layers such as skin and muscle in which extravasation is much less likely to occur.

While using RF electromagnetic power to detect extravasation and infiltration has thus been established as an effective approach, the present innovation addresses certain clinical aspects. Fluid injections, liquid infusions, and IV drips require that measures be taken to avoid infection. In particular, tubing and dressings are typically disposable and frequently replaced. Sensing extravasation or infiltration can entail placement of transmitters and receivers close to an insertion point on the skin of a patient. As such, a device for detecting extravasation or infiltration of fluids in the tissue can pose as a source of infection or contamination if not similarly disposable. However, circuitry for generating and analyzing RF electromagnetic signals typically entails use of digital signal processing equipment that can prove to be too expensive for single uses.

Thus, a passive sensor of a system is driven by transmitted RF electromagnetic power, passes the power through tissue of a body portion for detecting a level of fluid, and transmits back an output signal for remote digital signal processing. Thereby, a relatively inexpensive component implementation can be incorporated into the passive sensor. In certain clinical environments, more than one passive sensor can be driven by the transmitted RF electromagnetic power since the transmission in response can be delayed in time as well as being at a reduced power level.

Various aspects are now described with reference to the drawings. In the following description, for purposes of explanation, numerous specific details are set forth in order to provide a thorough understanding of one or more aspects. It may be evident, however, that such aspect(s) may be practiced without these specific details.

Figure 1:
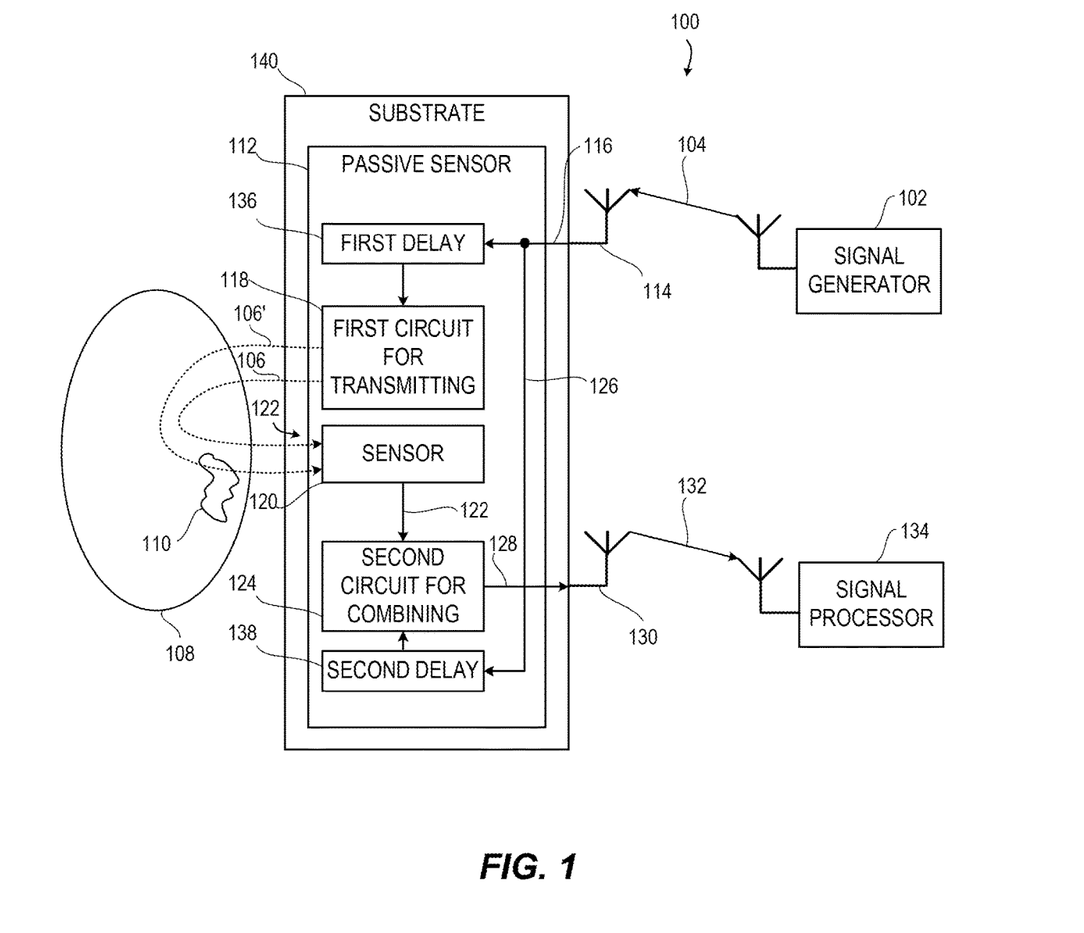
FIG. 1 is a schematic block diagram of a system for detecting a change in a fluid level in tissue using an RF driven passive sensor, according to one aspect.

In FIG. 1, the present disclosure provides a system 100 for detecting extravasation or infiltration. A signal generator 102 transmits a transmitted signal 104 comprising Radio Frequency (RF) electromagnetic power selected for being transmittable as depicted at 106 or 106' through a body portion 108 in relation to an amount of fluid 110 in the body portion 108 due to extravasation or infiltration.

A passive sensor 112 has a receiving antenna 114 for receiving the transmitted signal 104 as a received signal 116. The transmitted signal is split via a conventional splitter (not shown) into first and second portions. A first circuit 118 transmits the first portion of the received signal 116 through the body portion 108. A sensor 120 detects a resultant signal 122 from the body portion 108. The second portion of the received signal 116 travels through a reference pathway such as a delay line, wherein the second portion of the received signal is not affected by fluid or other changes in the tissue. A second circuit 124 combines the reference signal 126 comprising the second portion of the received signal 116 with the resultant signal 122 so as to define an output signal 128. A transmit antenna 130 transmits the output signal 132.

A signal processor 134 receives the transmitted output signal 132 as a received signal and uses the output signal 132 to determine a change in the fluid level within the body portion 108. In the illustrated embodiment, the signal processor compares a ratio of a peak amplitude of the resultant signal 122 to a peak amplitude of the reference signal 126, which ratio is determined from the output signal 132 during fluid injection into a patient body portion 108, with a ratio of a peak amplitude of a resultant signal to a peak amplitude of a reference signal taken earlier in time via the passive sensor 112 during a baseline detection operation, e.g., just before fluid is injected into the body portion 108. In FIG. 1, a first portion 106 of the received signal 104 corresponds to a signal being transmitted through the body portion 108 during a baseline operation and a first portion 106' of the received signal 104 corresponds to a signal being transmitted through the body portion 108 later in time when fluid has accumulated in the body portion 108 such that the first portion 106' passes through the accumulated fluid in the body portion 108.

In another aspect, the transmitted signal 104 further comprises a time domain pulse of electromagnetic power. The passive sensor 112 further comprises a first delay circuit 136 for delaying a selected one of the first portion of the received signal 116 comprising the time domain pulse and the second portion of the received signal comprising the time domain pulse as the reference signal 126. The second circuit 124 further combines the reference signal 126 with the resultant signal 122 comprising pulses separated as a function of time by the first delay circuit 136. In a particular aspect, a second delay circuit 138 delays the other one of the first portion and the second portion of the time domain pulse. The first and second delay circuits 136, 138 are configured to separate in time the resultant signal 122 and the reference signal 126 from each other as well as a noise pulse at the sensor 120 arising due to a reflected portion of the transmitted signal 104. Hence, there are two time delays for the first and second portions of the received signal 104. First, the two time delays are intentionally longer than room reflection delays so that the resultant signal 122 and the reference signal 126 can be separated from the room reflections in a final processing step. Second, the delay along the tissue pathway is intentionally different than the delay along the reference pathway, so that the resultant signal 122 and the reference signal 126 can be separated and analyzed. The delay along the reference pathway may be longer or shorter than the delay along the tissue pathway.

In another aspect, the receiving antenna 114 is further for receiving the transmitted signal 104 in a range of greater than 1.5 GHz to approximately 30 GHz over a period of time, and more particular the range is less than 10 GHz.

In an additional aspect, the passive sensor 112 includes a substrate 140 for supporting at least the receiving antenna 114, the first circuit 118 for transmitting, the second circuit 124 for combining, the sensor 120, and the transmit antenna 130.

Figure 2:
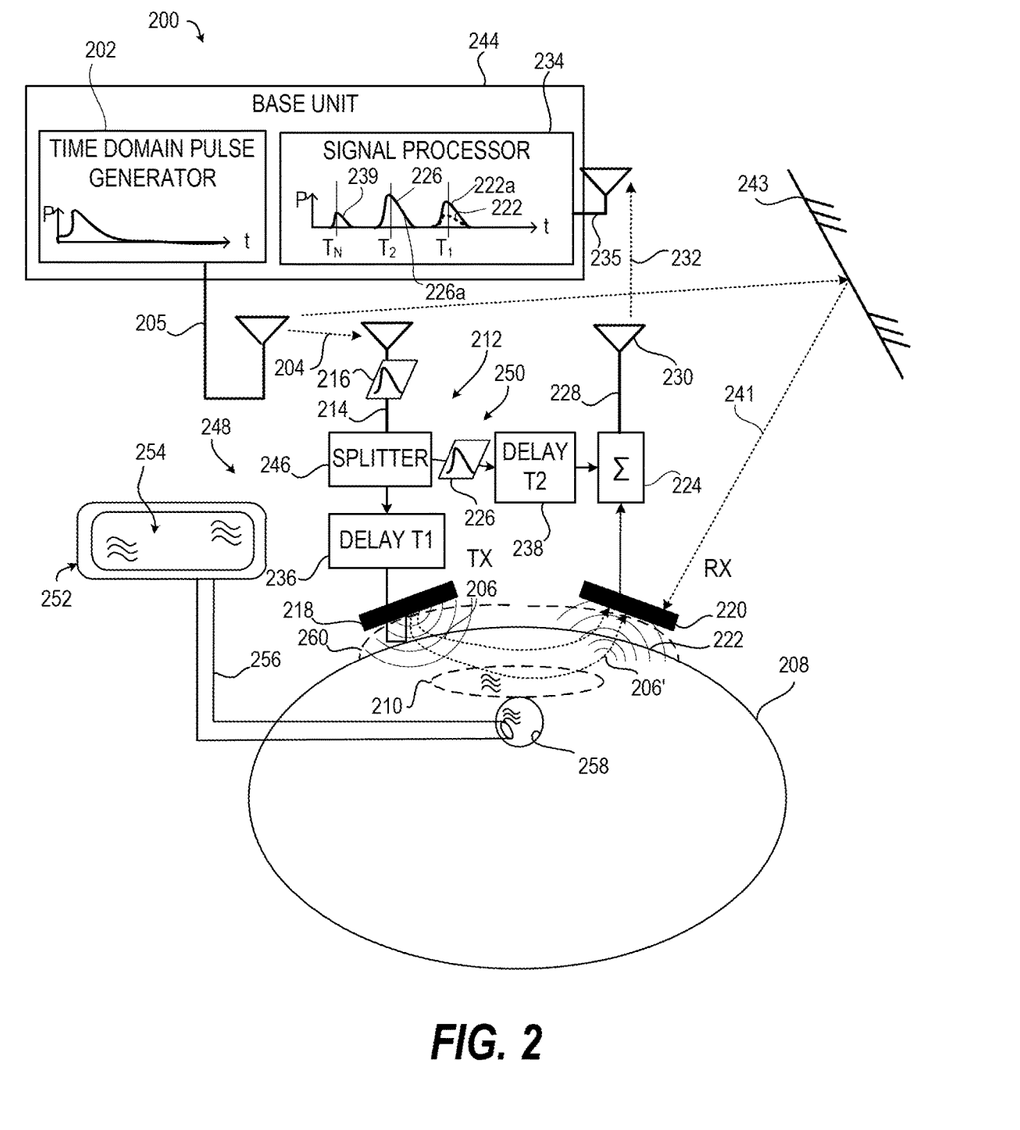
FIG. 2 is a schematic block diagram of a system for detecting a change in a fluid level using a time-domain RF pulse with combined and transmitted time-delayed reference and resultant signals for remote signal processing, according to one aspect.

In an exemplary aspect in FIG. 2, a system 200 has a signal generator 202, depicted as a time-domain pulse generator, that transmits a transmitted signal 204 as a time domain pulse via a transmit antenna(s) 205 to cause transmission as depicted at 206 or 206' through a body portion 208 in relation to an amount of fluid 210 in the body portion 208 due to extravasation or infiltration.

To that end, a passive sensor 212 has a receiving (RX) antenna(s) 214 for receiving the transmitted signal 204 (time domain pulse) as a received pulse or received signal 216. Thus, the passive sensor 212 comprises the RX antenna(s) 214 that receives a time domain impulse stream from a base unit 244 that includes the signal generator 202. This base unit 244 uses time domain or ultra-wideband radar methods to generate a series of impulses to be sent to the passive sensor 212. The passive sensor 212 then comprises a splitter 246 that splits first and second portions of the received signal 216 from the RX antenna(s) 214, respectfully, to a pathway 248 that will include the tissue of interest for sensing fluid 210 and a pathway 250 that returns the second portion of the signal back to the base unit 244.

A first circuit 218 comprising a transmit antenna(s) transmits the first portion of the received signal 216 through the body portion 208. A sensor 220 comprising a receiving antenna(s) detects a resultant signal 222 from the body portion 208. A second circuit 224 combines the second portion of the received signal 216, which second portion defines a reference signal 226, with the resultant signal 222 so as to define an output signal 228. A transmit antenna(s) 230 transmits the output signal 228 as a transmitted output signal 232.

A signal processor 234 serves as an extravasation/infiltration detector by receiving the transmitted output signal 232 at a receiving antenna(s) 235 as a received signal and for comparing a patient fluid injection ratio of the resultant signal 222 to the reference signal 226 taken during patient fluid injection to a baseline ratio of a resultant signal to a reference signal generated earlier in time during a baseline detection operation so as to detect a change from the baseline ratio, which change corresponds to a change in the fluid level in the body portion 208. If the patient fluid injection ratio is less than a predefined percentage of the baseline ratio, e.g., 90% of the baseline ratio, then this can warrant an alert indicating that an unacceptable fluid level change has occurred. In FIG. 2, a first portion 206 of a received signal corresponds to a signal being transmitted through the body portion 208 during the baseline operation and a first portion 206' of a received signal 204 corresponds to a signal being transmitted through the body portion 208 later in time when fluid 210 has accumulated in the body portion 208 such that the first portion 206' passes through the accumulated fluid 210 in the body portion 208.

In the exemplary implementation, the passive sensor 212 further comprises a first delay circuit 236 depicted as a delay line T1, for delaying the first portion of the received signal 216 by a time "T1" prior to transmission through the body portion 208 so as to ensure that the first portion lags the second portion of the received signal 216. In a particular aspect, a second delay circuit 238 delays the reference signal 226 such that the reference signal 226 is separated in time, i.e., follows a noise pulse 239 at the sensor 220 arising due to a reflected portion 241 of the transmitted signal 204 from an ambient environment 243, see FIG. 2. In the illustrated embodiment, time $T1+T_T$ (signal delay in a patient body portion) is greater than time T2. However, it is contemplated that time T2 may be greater than $T1+T_T$.

Hence, both pathways 248, 250 illustrated in FIG. 2 have first and second delay circuits 236, 238 (delay line T1 and delay line T2). The delay line T1 (first delay circuit 236) is present so that the signal that propagates through the tissue will lag behind the T2 pathway signal. Delay line T2 (second delay circuit 238) allows room reflections to complete before the transmitted reference signal 226 is returned to the signal processor 234 of the base unit 244. Thus, the shorter pathway provides the reference signal 226 that is independent of the tissue/fluid effects, but will include effects of distance changes between the passive sensor 212 and the base unit 244. Thereby, the system 200 looks for relative changes between the ratio of the current resultant signal 222 to the current reference signal 226 to a baseline ratio of a resultant signal 222A to a reference signal 226A generated earlier in time during a baseline detection operation so as to detect a change from the baseline ratio, which change corresponds to a change in the fluid level in the body portion 208. If the sensor 212 moves away from the base unit 244, both the current resultant signal 222 and the current reference signal 226 will decrease by the same percentage such that the ratio remains constant. If a fluid accumulation occurs within the body portion 208, the ratio of the current resultant signal 222 to the current reference signal 226 will change relative to the baseline ratio.

In use, a fluid supply 252 (e.g., infuser supply, contrast agent injector, IV drip, etc.) provides fluid 254 via a conduit 256 (e.g., catheter, needle, etc.) to a vascular body 258 of the body portion 208. As depicted at 210, extravasation or infiltration can cause an increase in a level of fluid that directly affects a signal 206' propagating through the tissue, such as based in a change in permittivity. For example, if the current reference signal 226 during patient fluid injection equals the baseline reference signal 226A and an increase in fluid level has occurred in the patient, then the current resultant signal 222 during patient fluid injection will typically be less than the baseline resultant signal 222A, see FIG. 2. A resulting change in dimensions of the body portion 208, as depicted at 260, can cause a change in the signal 206'.

Figure 3:
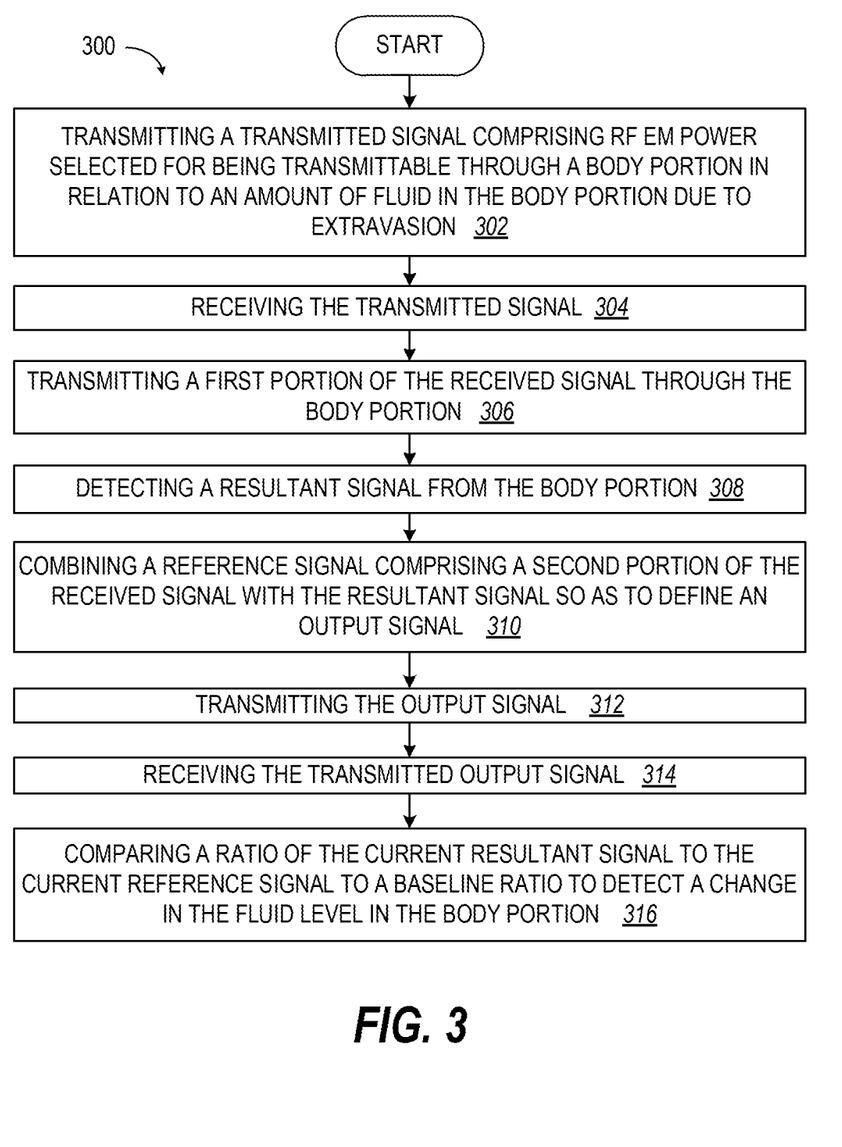
FIG. 3 is a flow diagram of a methodology for detecting a change in the fluid level of tissue, according to one aspect.

In FIG. 3, a method 300 for detecting extravasation or infiltration is depicted. A transmitted signal is transmitted comprising RF electromagnetic power selected for being transmittable through a body portion in relation to an amount of fluid in the body portion due to extravasation or infiltration (block 302). The transmitted signal is received as a received signal (block 304). A first portion of the received signal is transmitted through the body portion (block 306). A resultant signal is detected from the body portion (block 308). A reference signal comprising a second portion of the received signal is combined with the resultant signal so as to define an output signal (block 310). The output signal is transmitted (block 312). The transmitted output signal is received (block 314). A ratio of the current resultant signal to the current reference signal is compared to a baseline ratio to detect a change in the fluid level in the body portion (block 316).

In another exemplary aspect, the transmitted signal further comprises a time domain pulse of electromagnetic power. The method further comprises delaying a selected one of the first portion of the received signal comprising the time domain pulse and a second portion of the received signal comprising the time domain pulse as the reference signal. The reference signal is combined with the resultant signal as pulses separated as a function of time. In a particular aspect, the other one of the first portion and the second portion of the time domain pulse is delayed to separate in time the resultant signal and the reference signal from each other as well as blanking a noise pulse arising due to a reflected portion of the transmitted signal from an ambient environment.

In an additional exemplary aspect, the transmitted signal is transmitted in a range of greater than 1.5 GHz to approximately 30 GHz over a period of time. In a particular aspect, the range is less than 10 GHz.

In a further exemplary aspect, a user indication is presented of a selected one of an inoperative state, a nominal state and an extravasation state based upon the comparison.

In an alternative embodiment, the signal generator is a continuous wave (CW) source, which generates and transmits continuous wave power swept across a frequency range such as 2 GHz to 5 GHz (remaining at each frequency long enough for an amplitude and phase measurement by the receiving circuitry to be made, which is typically a fraction of a second). In the continuous wave embodiment, the passive sensor is generally the same as the passive sensor in the pulse source embodiment, discussed above. Hence, the passive sensor comprises a splitter for splitting continuous wave power into first and second portions, first and second delays for delaying (i.e., introducing differing phase shifts) the first and second portions different amounts, a first circuit comprising transmit and receive antennas and a second circuit for combining a resultant signal, which is defined by the second portion of the continuous wave power after passing through tissue, and a reference signal, which is defined by the first portion of the continuous wave power. Amplitude and phase data for a plurality of frequencies, e.g., 256 frequencies, of the combined signal are provided to a signal processor, which converts the frequency domain information from the combined signal into the time domain using inverse-Fourier or other transforms known in the art. Once in the time domain, the processor determines a first ratio of a peak amplitude of the resultant signal to a peak amplitude of the reference signal, which ratio is determined from the combined signal output during fluid injection into a patient body portion. The processor also determines a second ratio of a peak amplitude of a resultant signal to a peak amplitude of a reference signal taken earlier in time during a baseline detection operation, e.g., just before fluid is injected into the body portion. The processor then compares the first and second ratios to one another to detect a change in a fluid level in a body portion.

While the foregoing disclosure discusses illustrative aspects and/or embodiments, it should be noted that various changes and modifications could be made herein without departing from the scope of the described aspects and/or embodiments as defined by the appended claims. Furthermore, although elements of the described aspects and/or embodiments may be described or claimed in the singular, the plural is contemplated unless limitation to the singular is explicitly stated. Additionally, all or a portion of any aspect and/or embodiment may be utilized with all or a portion of any other aspect and/or embodiment, unless stated otherwise.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein, will only be incorporated to the extent that no conflict arises between that incorporated material and the existing disclosure material.

What is claimed is:

1. A system for detecting extravasation, comprising:
   a signal generator for transmitting a transmitted signal comprising Radio Frequency (RF) electromagnetic power;
   a passive sensor, comprising:
      a receiving antenna configured to receive the transmitted signal as a received signal,
      a first circuit configured to transmit only a first portion of the received signal through the body portion,
      a sensor configured to detect a resultant signal from the body portion,
      a second circuit configured to combine a reference signal comprising a second portion of the received signal with the resultant signal so as to define an output signal, and
      a transmit antenna configured to transmit the output signal as a transmitted output signal; and
   a signal processor configured to:
      receive the transmitted output signal, and
      perform a comparison of peak amplitude of resultant signal and the reference signal of the transmitted output signal to detect extravasation of fluid in the body portion by determining a change in fluid level in the body portion using the transmitted output signal,
   wherein the transmitted signal further comprises a time domain pulse of electromagnetic power, and
   wherein the passive sensor further comprises:
   (i) a first delay circuit configured to delay a selected one of the first portion of the received signal comprising the time domain pulse and the second portion of the received signal comprising the time domain pulse as the reference signal, and
   (ii) a second delay circuit configured to delay the other one of the first portion and the second portion of the time domain pulse, the first and second delay circuits being configured to separate in time the resultant signal, the reference signal, and a noise pulse at the sensor arising due to a reflected portion of the transmitted signal.

2. The system of claim 1, wherein the receiving antenna is further configured to recieve the transmitted signal in a range of greater than 1.5 GHz to approximately 30 GHz over a period of time.

3. The system of claim 1, wherein the transmitted signal comprises a sweep of continuous wave electromagnetic power across a frequency range.

4. The system of claim 1, further comprising a substrate configured to support said receiving antenna, said first circuit, said second circuit, said sensor, and said transmit antenna.

5. A method for detecting extravasation, comprising:
transmitting, by a signal generator, a transmitted signal comprising Radio Frequency (RF) electromagnetic power;
received, by a receiving antenna of a passive sensor, the transmitted signal as a received signal;
transmitting, by a first circuit of the passive sensor, only a first portion of the received signal through a body portion;
detecting, by a sensor of the passive sensor, a resultant signal from the body portion;
combing, by a second circuit of the passive sensor, a reference signal comprising a second portion of the received signal with resultant signal to define an output signal;
transmitting, by a transmit antenna of the passive sensor, the output signal as a transmitted output signal;
receiving, by the signal processor, transmitted output signal;
performing, by the signal processor, a comparison of peak amplitude of the resultant signal and the reference signal; and
detecting, by signal processor, extravasation of fluid in the body portion by determining a change in fluid level in the body portion using the transmitted output signal,
wherein the transmitted signal further comprises a time domain pulse of electromagnetic power, the method further comprising:
delaying, by a first delay circuit of the passive sensor, a selected one of the first portion of the received signal comprising the time domain pulse and the second portion of the received signal comprising time domain pulse as the reference signal; and
delaying, by a second delay circuit of the passive sensor, the other one of the first portion and the second portion of the time domain pulse, wherein the first and second delay circuits are configured to separate in time the resultant signal, the reference signal, and a noise pulse at the sensor arising due to a reflected portion of the transmitted signal.

6. The method of claim 5, further comprising:
combining, by the second circuit of the passive sensor, the reference signal with the resultant signal as pulses separated as a function of time.

7. The method of claim 5, further comprising:
transmitting, by the signal generator, the transmitted signal in a range of greater than 1.5 GHz to approximately 30 GHz over a period of time.

8. The method of claim 5, wherein the transmitted signal comprises a pulse of continuous wave electromagnetic power across a frequency range.

9. The method of claim 5, wherein the reference signal is not affected by fluid in the body portion.

10. the method of claim 5, further comprising splitting, by a signal splitter of the passive sensor, the transmitted signal into the first portion and the second portion, the second portion defining the reference signal.

* * * * *

UNITED STATES PATENT AND TRADEMARK OFFICE
CERTIFICATE OF CORRECTION

PATENT NO. : 10,722,136 B2
APPLICATION NO. : 14/241179
DATED : July 28, 2020
INVENTOR(S) : Chad E. Bouton It is certified that error appears in the above-identified patent and that said Letters Patent is hereby corrected as shown below:

In the Claims

Column 10, Line 29, Claim 1, "through the body portion," should read --through a body portion,--

Column 10, Line 40, Claim 1, "amplitude of resultant" should read --amplitude of the resultant--

Column 10, Line 62, Claim 2, "further configured to recieve" should read --further configured to receive--

Column 11, Line 9, Claim 5, "received, by a receiving antenna" should read --receiving, by a receiving antenna--

Column 11, Line 16, Claim 5, "combing, by a second circuit" should read --combining, by a second circuit--

Column 11, Line 18, Claim 5, "signal with resultant" should read --signal with the resultant--

Column 11, Line 22, Claim 5, "receiving, by the signal processor, transmitted output" should read --receiving, by a signal processor, the transmitted output--

Column 11, Line 27, Claim 5, "detecting, by signal processor" should read --detecting, by the signal processor--

Column 12, Line 22, Claim 8, "pulse of continuous wave" should read --sweep of continuous wave--

Signed and Sealed this
Eleventh Day of May, 2021

Drew Hirshfeld
*Performing the Functions and Duties of the
Under Secretary of Commerce for Intellectual Property and
Director of the United States Patent and Trademark Office*